United States Patent [19]
Sikkema

[11] Patent Number: 5,945,537
[45] Date of Patent: Aug. 31, 1999

[54] NITRATION OF PYRIDINE-2, 6-DIAMINES

[75] Inventor: Doetze Jakob Sikkema, Oosterbeek, Netherlands

[73] Assignee: Akzo Nobel N.V., Arnhem, Netherlands

[21] Appl. No.: 09/041,882

[22] Filed: Mar. 12, 1998

Related U.S. Application Data

[63] Continuation of application No. PCT/EP96/03841, Sep. 2, 1996.

[30] Foreign Application Priority Data

Sep. 19, 1995 [NL] Netherlands ............................ 1001238

[51] Int. Cl.$^6$ .................................................. C07D 213/02
[52] U.S. Cl. ................................................................ 546/307
[58] Field of Search ............................................... 546/307

[56] References Cited

U.S. PATENT DOCUMENTS

| | | | |
|---|---|---|---|
| 4,310,671 | 1/1982 | Boudakian | 546/304 |
| 4,560,800 | 12/1985 | Bakshi et al. | 568/306 |

FOREIGN PATENT DOCUMENTS

| | | |
|---|---|---|
| 3920336 | 1/1991 | Germany . |
| WO 94/25506 | 11/1994 | WIPO . |

OTHER PUBLICATIONS

Derwent Patent Abstract No. 91–015456 [03] (1991).

Derwent Patent Abstract No. 94–290874/36 (1994).

R.L. Williams et al., "The Chemistry of Aryltetraamines. II. The Synthesis of 2,3,5,6–Tetraaminopyridine", J. Heterocyclic Chem., 8 (Oct. 1971), pp. 841–843.

H. Ritter et al., "Synthesis and Reactions of Dinitrated Amino and Diaminopyridines", J. Heterocyclic Chem., 32 (Mar.–Apr. 1995), pp. 585–590.

H.–H. Licht et al., "Novel Explosives: Dinitropyridines", Nit. Annu. Conf. ICT(1993), 24$^{th}$ (Energetic Materials: Insensitivity and Environmental Awareness), pp. 6/1–6/8.

*Primary Examiner*—Zinna Northington Davis
*Attorney, Agent, or Firm*—Richard P. Fennelly

[57] ABSTRACT

It has been found that the nitration of pyridine-2,6-diamines, which is commonly performed in a mixture of nitric acid and concentrated sulfuric acid, will give a significantly higher yield (from about 50% up to more than 90%) if the reaction is carried out in a mixture of nitric acid and oleum, or by otherwise providing an inherently anhydrous medium.

4 Claims, No Drawings

NITRATION OF PYRIDINE-2, 6-DIAMINES

The present application is a Continuation of International Application No. PCT/EP96/03841 filed Sep. 2, 1996.

BACKGROUND OF THE INVENTION

The invention pertains to a process for preparing nitrated pyridine-2,6-diamines in which a pyridine-2,6-diamine is contacted with a mixture of nitric acid and sulfuric acid. By the term "pyridine-2,6-diamines" are meant 2,6-diaminopyridine (DAP) and derivative compounds with substitution in the pyridine ring of either or both amino groups and/or carbon atom no. 4 (C-4).

The resulting 2,6-diamino-3,5-dinitropyridine (DADNP) is a suitable starting material for the manufacture of monomers for rigid rod polymers such as described in PCT Published Patent Application WO 94/25506 (reduction of the two nitro groups produces the desired tetra-amine). DADNP can also be used as an insensitive (safe) explosive and as a multifunctional organic reagent.

The nitration of DAP by having it react with a mixture of nitric acid and sulfuric acid is known from German Patent Publication No. 3,920,336. The drawback to this process is that it gives a DADNP yield of not more than 50% of theory.

Another disclosure of the nitration of DAP by reacting it with a mixture of sulfuric acid and nitric acid is Williams et al., J. Heterocyclic Chem., 8, 841–843 (1971). Williams discloses the use of concentrated sulfuric acid and a small amount of 90% nitric acid. Yield data other than for crude product are not given.

Further background art is Ritter et al., J. Heterocyclic Chem., 32, 585 (1995), which mentions the nitration of DAP using nitric acid and indicates the occurrence of by-product formation.

In view of the above it is desired to come up with a DAP nitration process which will produce a higher yield and so offer greater economic advantage as well as making for lower amounts of waste material.

DESCRIPTION OF THE INVENTION

The invention therefore has for its object to provide as economic process by which pyridine diamines can be nitrated with a good yield of neat product, without substantial by-products. To this end the invention consists of a process of the known type mentioned in the opening paragraph in which the sulfuric acid is meant according to the invention; over 100% -sulfuric acid (actually, a solution of sulfur trioxides in 100% sulfuric acid which is also known as oleum).

It should be noted that nitration with a mixture of nitric acid (usually 100% nitric acid) and oleum as such is known. However, it cannot be derived from the background information that this specific mixture is capable of solving the above-described problem. For instance, U.S. Pat. No. 4,310,671 discloses the nitration of 2,6-dichloropyridine in oleum. However 2,6-dichloropyridine nitration and DAP nitration cannot be compared. This is clear, for example, from the fact that with DAP it is a question of dinitration, while 2,6-dichloro-pyridine is subject only to mono-nitration reaction. Moreover, the 2,6-dichloropyridine nitration is achieved only with difficulty, so it is not surprising that, in general, a powerful nitrating agent is selected. In the case of DAP this option is not at all obvious, given that the dinitration as such proceeds easily and the low yield cannot be explained just like that either.

Further background includes Japanese Patent Publication No. Hei-6-220019, from which it is known to nitrate 2-hydroxypyridine with a mixture of fuming nitric acid and concentrated sulfuric acid or oleum, and U.S. Pat. No. 4,560,800, from which it is known to prepare 3,5-dinitrobenzophenone by nitrating benzophenone and a mixture of nitric acid and oleum. In H. H. Licht et al., Int. Annu. Conf. ICT (1993), 24th (Energetic Materials: Insensitivity and Environmental Awareness), 6-1/6-8, DADNP is made by nitrating DAP with nitric acid and concentrated sulfuric acid in a number of steps.

The finding that nitration with oleum gives a surprisingly higher yield, well in excess of 90%, may lead one to surmise, without wishing to be bound by this theory, that it was the exclusion of water which led to reduced degradation by hydrolysis of the nitration products which were easy to form as such. In this connection, the invention also relates to the nitration reaction of pyridine-2,6-diamines in which a pyridine-2,6-diamine is contacted with a nitrating agent in the form of a mixture of nitric acid and sulfuric acid, but where the presence of water is countered in a different fashion, e.g., by carrying out the reaction in an inherently anhydrous medium (i.e., a medium where the released water is trapped by a compound which is more strongly hygroscopic than the nitration product formed during the reaction), e.g., in the presence of polyphosphoric acid, diphosphorus pentoxide, acetic anhydride, and the like.

The process according to the present invention is preferably carried out in oleum having a sulfur trioxide concentration of 20 to 65%. The sulfur trioxide percentage does not have any real effect on the results. The use of 20%-oleum is preferred for practical reasons. According to the present invention, it is possible to use oleum as commercially available. Alternatively, use may be made of concentrated sulfuric acid with 20%- or 65%-oleum added thereto to obtain the desired fuming sulfuric acid concentration. Theoretically, it is possible to start from less concentrated sulfuric acid and to add a larger quantity of sulfur trioxide, but in so far as free sulfur trioxide can be handled at all, it is preferred not to do so for practical reasons. The final concentration of the (fuming) sulfuric acid exceeds 100% and is preferably 104.5 to 114.5%.

Preferably, the nitric acid used in the process according to the invention is concentrated (over 95%), more preferably still, 100% nitric acid is employed. When lower concentrations of nitric acid are used, it is preferred to employ oleum having a high sulfur trioxide content. The favorable effect of this is that on conclusion of the nitration reaction the sulfuric acid is still virtually free of water. The most favorable results are achieved when the fuming sulfuric acid has a concentration of more than 104% (which corresponds to 20%-oleum) and the nitric acid has a concentration of more than 97%.

It is preferred to use not more than 2.1 moles of nitric acid per mole of DAP and to carry out the reaction at a temperature of less than 30° C., preferably between 15° C. and 25° C. If during treatment the nitrated product precipitates because the intensely acidic medium is diluted with water, it is recommended to keep the contact time between the reaction product in solution and the water as brief as possible (preferably less than five seconds), and maintain a low temperature during said contact (preferably less than 25° C.).

If so desired, instead of DAP itself there may be used in the process according to the present invention derivative compounds with substitution in the pyridine ring of either or both amino groups and/or carbon atom no. 4 (C-4) with oleum-resistant substituents. General knowledge of the field will enable the skilled person to select suitable substituents, e.g., alkyl, especially lower alkyl such as $C_{1-6}$ alkyl, haloalkyl, aralkyl, notably deactivated aralkyl such as nitrotoluenyl.

The invention will be further elucidated with reference to the following non-limiting Examples which follow.

EXAMPLE 1

In a 3-liter reactor equipped with a rapid stirrer, a large bore neck for solids addition, and a dropping funnel, which was protected against atmospheric moisture entry, 1200 ml of 20%-oleum were cooled to 15° C.

In small portions, 2.75 moles (300.1 g) of DAP were added (with quick reclosing of the neck after each addition): this took ninety minutes, and the temperature remained below 25° C., mostly below 20° C. After further stirring for fifteen minutes 240 ml of 100%-nitric acid were slowly added over a period of one hundred and thirty minutes at 18–20° C. In all, about 6 kg of ice were used for cooling during the dissolution and nitration steps. After another ten minutes of stirring with cooling, the somewhat viscous, dark red, clear reaction mixture was stirred into 7 kg of ice; the final temperature of the coagulation mixture was 1.5° C.

The solids were filtered off, were washed three times with 1 l of water, and were dried for forty-eight hours at 50° C., 1 mbar. The yield was 2,483 moles, 90.3% DADNP. Pouring out said reaction mixture containing a greater excess of ice gave a better yield still, 94%.

EXAMPLE 2

The nitration reaction of Example 1 was performed in a 1-liter reactor at ⅓ scale (somewhat shorter times were needed because of the larger specific cooling area) using ice-water cooling. Towards the end of the nitration a 3-liter three-necked flask equipped with a rapid stirrer, a dropping funnel, and a vacuum outlet was charged with 2.5 l of methanol, which was cooled to 10° C. by evacuation and boiling in vacuo. Using the dropping funnel, the reaction mixture was stirred into the cold methanol boiling in vacuo in forty minutes at 9–12° C. The resulting slurry was filtered off and was stirred into 1 l of ice/water; the new precipitation was filtered off, washed three times with water, and dried for thirty hours at 50° C. and 1 mbar to give a yield of 150.67 g of product, 82.5%. It should be noted that this yield of 82.5% in the synthesis indicates the presence of virtually all of the theoretical amount of nitration product in the reaction mixture. This was confirmed with the aid of a comparable methanol filtrate: the precipitation with methanol of a sample of pure nitrated product (DADNP) in 100% sulfuric acid, collection of the solids at 10° C., and washing with water gave a yield of 83% of the product. Successful recovery of the sulfuric acid and the product in the methanol filtrate thus makes for a quantitative yield in the case of production on a (semi) commercial scale.

I claim:

1. A process for preparing nitrated pyridine-2,6-diamines in which a pyridine-2,6-diamine is contacted with a mixture of nitric acid and sulfuric acid, wherein the sulfuric acid used is fuming sulfuric acid (oleum).

2. A process according to claim 1, wherein the oleum has a sulfur trioxide concentration of 20 to 65%.

3. A process according to claim 1, wherein the fuming sulfuric acid has a concentration of more than 104% and the nitric acid has a concentration of more than 97%.

4. A process for preparing nitrated pyridine-2,6-diamines in which a pyridine-2,6-diamine is reacted with a mixture of nitric acid and sulfuric acid, wherein the nitration reaction is carried out in an inherently anhydrous medium.

* * * * *